United States Patent
Steen

(10) Patent No.: US 6,558,411 B1
(45) Date of Patent: *May 6, 2003

(54) DEVICE FOR ILLUMINATING A DEFINED AREA

(75) Inventor: Harald B. Steen, Oslo (NO)

(73) Assignee: Photocure ASA, Oslo (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,736

(22) PCT Filed: May 11, 1998

(86) PCT No.: PCT/NO98/00144

§ 371 (c)(1),
(2), (4) Date: Nov. 12, 1999

(87) PCT Pub. No.: WO98/52205

PCT Pub. Date: Nov. 19, 1998

(30) Foreign Application Priority Data

May 15, 1997 (NO) ................................................ 972244

(51) Int. Cl.[7] .............................................. A61N 5/006
(52) U.S. Cl. ............................ 607/88; 607/90; 607/91; 606/9
(58) Field of Search .................... 607/88–91, 93, 607/94, 96; 606/2, 9, 10, 13, 16–18; 128/898

(56) References Cited

U.S. PATENT DOCUMENTS

| | | | | |
|---|---|---|---|---|
| 3,535,507 A | | 10/1970 | Sugino | 240/41.3 |
| 3,693,623 A | * | 9/1972 | Harte et al. | 128/303.1 |
| 4,787,013 A | | 11/1988 | Sugino et al. | 362/32 |
| 5,320,618 A | * | 6/1994 | Gustafsson | 606/9 |
| 5,344,433 A | | 9/1994 | Talmore | 607/88 |
| 5,407,808 A | * | 4/1995 | Halling et al. | 435/35 |
| 5,425,754 A | * | 6/1995 | Braun et al. | 607/88 |
| 5,554,153 A | * | 9/1996 | Costello et al. | 606/9 |
| 5,653,706 A | * | 8/1997 | Zalvislan et al. | 606/9 |
| 5,720,772 A | * | 2/1998 | Eckhouse | 607/88 |
| 5,755,751 A | * | 5/1998 | Eckhouse | 607/88 |
| 5,759,200 A | * | 6/1998 | Azar | 607/89 |
| 5,885,274 A | * | 3/1999 | Fullmer et al. | 606/9 |
| 5,947,957 A | * | 9/1999 | Morris | 606/13 |
| 5,961,543 A | * | 10/1999 | Waldmann | 607/88 |

FOREIGN PATENT DOCUMENTS

| | | |
|---|---|---|
| DE | 2421181 | 2/1975 |
| EP | 731485 B1 | 9/1996 |
| EP | 752254 A1 | 1/1997 |
| EP | 765674 A2 | 4/1997 |
| HU | 191836 | 11/1983 |
| RU | 2053532 | 1/1996 |
| RU | 2100823 | 4/1997 |
| RU | 2097807 | 11/1997 |

* cited by examiner

Primary Examiner—Linda C. M. Dvorak
Assistant Examiner—Ahmed Farah
(74) Attorney, Agent, or Firm—Kenyon & Kenyon

(57) ABSTRACT

A device for irradiating a limited, defined area where uniform and intense irradiation is obtained of a sharply defined light field (7) of variable size, the light from a halogen lamp (1) or similar incoherent light source being directed by means of an elliptical mirror (2) towards one end surface (3) of a transparent rod (4) whose opposite end surface (6) is thereby uniformly irradiated and is imaged by a lens (7) in the area (9) which has to be irradiated.

11 Claims, 1 Drawing Sheet

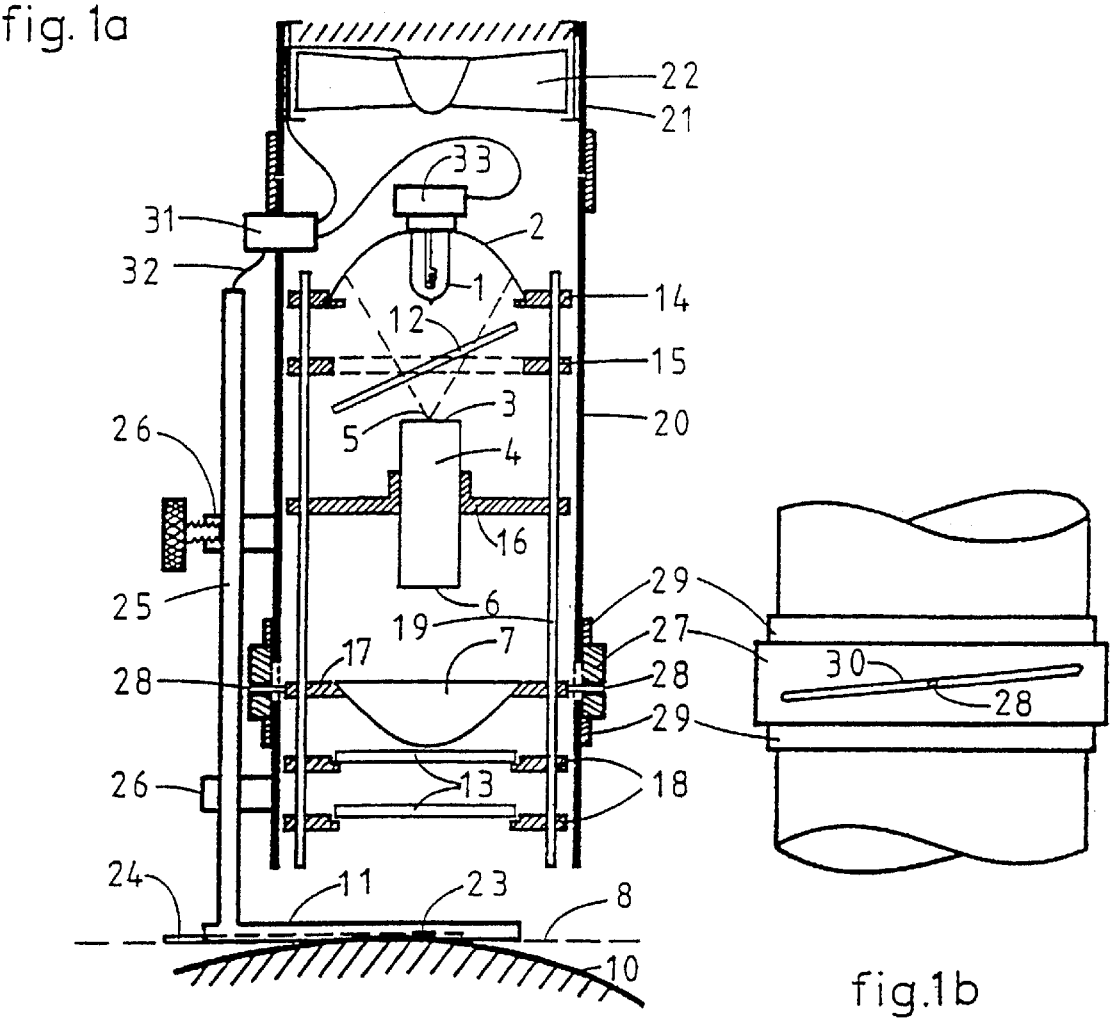
fig.1a
fig.1b
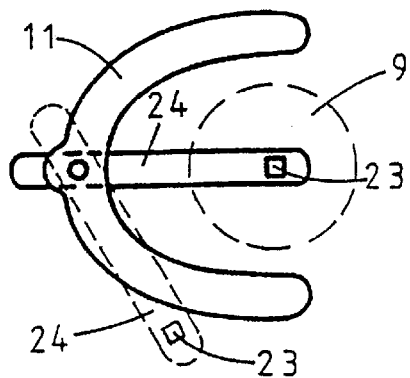
fig.1c

DEVICE FOR ILLUMINATING A DEFINED AREA

The present invention concerns a device for illuminating a limited, defined area (hereinafter called "light field"), e.g. cancerous tumours and other pathological skin conditions which can be treated by this method, comprising a light source with a reflector device together with light-conducting means. The device satisfies the demands for intensity and uniformity of the irradiation, while being so inexpensive, small, light and mobile that it can also be employed in the outpatients' department.

Photochemical treatment has been shown to be a highly promising form of treatment for certain types of skin cancer, especially basal cell carcinoma, as well as some other skin disorders such as psoriasis. In this treatment a photosensitising compound, i.e. a substance which has little or no inherent toxicity, is applied to the tissue which is to be treated. Upon illumination highly reactive chemical species are produced, especially singlet oxygen. Thus, in subsequent illumination of the tissue the light-exposed cells which contain sufficient quantities of the photosensitising compound are killed. Certain types of photosensitising compounds, including certain porphyrins, have much greater affinity to cancerous tissue than to normal skin tissue. The treatment can therefore be directed specifically to the cancerous tissue, partly by means of the photosensitising substance's greater affinity with such tissue and partly by directing the irradiation solely on to this tissue. This type of treatment is now in routine use in several hospitals all over the world.

For the photosensitising compounds in use to-day, light with a wavelength in the range 600–700 nm is normally employed. The amounts of light required for such treatment are relatively large, i.e. of the magnitude 50–100 $J/cm^2$, which is normally supplied for a period of 5 to 10 minutes, i.e. with a fluence of approximately 100–200 $mW/cm^2$. Laser light has therefore normally been used. Due to the high intensity required, very large lasers have to be employed, normally a Cu laser coupled to a dye laser set, e.g., at 630 nm. Lasers of this kind are very expensive both with regard to purchase and operation, they require specially trained personnel and they are not mobile. Since photochemical treatment of skin diseases is preferably carried out in the outpatients' department and generally outside hospitals, there is a need for a light source which is inexpensive, can be used without extensive training and is easy to move. Furthermore, it is important for the area which is irradiated to be sharply defined, thus avoiding exposure of surrounding tissue. In addition, it is important that the fluence of the light should be approximately constant across the entire light field. Attempts have been made to replace the laser with a conventional light source, preferably a halogen lamp. However, it has proved difficult to combine high light intensity with uniform irradiation over a sharply defined and sufficiently large light field. Moreover, the light distribution from such light sources will be highly dependent on precise positioning of the incandescent element to the mirror or other optical device which collects and focuses the light, since the large aperture which this optical device must have in order to collect a sufficiently large portion of the light entails the necessity for a very high magnification. Since the mechanical reproducibility of halogen lamps is limited, this entails a not inconsiderable readjustment of the optics/lamp when the lamp is replaced. The invention which is described herein solves this problem as well as fulfilling the said requirements for intensity and uniformity of the light field. Furthermore, it enables the size of the light field to be varied in a simple manner.

The invention is characterized by the features which are presented in the independent claim 1 together with the dependent claims.

BRIEF DESCRIPTION OF THE DRAWINGS

FIG. 1a is a cross-sectional side view that illustrates a device for illuminating a defined area, according to one embodiment of the present invention;

FIG. 1b is a side view of the device illustrated in FIG. 1a; and

FIG. 1c is a bottom view of the device illustrated in FIG. 1a.

The invention comprises a light source 1, for example a halogen lamp, which is placed in one focus of a reflector device, e.g. an elliptical mirror 2. The light is directed towards one end surface 3 of a rod 4 of glass or another transparent material, the axis of which coincides with that of the mirror 2 and its end surface 3 in the mirror's second focus 5. In this manner an approximately uniform illumination of the rod's second end surface 6 is obtained. This end surface is imaged by a lens 7 in the plane 8 which is to be irradiated. The light field 9 is thereby uniformly irradiated. Since the end surface 6 will be uniformly illuminated regardless of where on the end surface 3 the light's focus 5, i.e. the image of the lamp's incandescent element, falls, the intensity distribution in the light field 9 and the light field's position will not be dependent on the lamp's exact position.

The rod 4 preferably consists of a material which absorbs infrared radiation. Between the mirror 2 and the rod 4 there is mounted a heat-reflecting mirror 12.

In the light path behind the lens 7 there are mounted one or more optical filters 13 which define the part of the spectrum which is to be employed in the illumination. The lamp 1 with the mirror 2, the heat-reflecting mirror 12, the rod 4, the lens 7 and the filters 13 are mounted in plates 14–18 provided on rails 19 which form a stand for these parts, one or more of the plates being movable on the rails. The stand with these parts is mounted in a tube 20. To this tube a second tube 21 is joined in which there is installed a fan 22, which draws air through the tubes 20 and 21. The latter tube 21 may be dismantled from the former tube, thereby facilitating the replacement of the lamp 1 and possibly the mirror 2.

The size of the light field can be adjusted by moving the lens 7, thereby altering the distance between the lens 7 and the end surface 6 of the rod 4. The distance between the lens 7 and the end surface 6 of the rod 4 can be altered by providing the plate 17 which carries the lens 7 with two pins 28 which run in a tilted groove 30 in the ring 28. The ring 28 can be rotated about the axis of the tube 20, since it runs between two fixed rings 29. When the extent of the light field is altered in this way, the distance to the light field 9 is also altered. In order to stabilize the lamp at the correct distance in relation to the skin 10 which has to be treated, the device is equipped with a foot 11 which is placed against the skin 10. The foot 11 is mounted on a tube 25 which runs through brackets 26 attached to the tube 20, thus enabling the distance between the foot and the device also to be adjusted so that the underside of the foot coincides with the plane 8.

The lamp 1 is supplied with stabilized voltage to the socket 33 through the contact 31. Current is also supplied through the contact 31 to the fan 22. The signal from the photo-diode is supplied through the same contact 31 via a wire 32 which is passed through the tube 25 from the arm 24 in the foot 11. On the foot 11 a photo-diode 23 is mounted on an arm 24 which can be moved, thus enabling the photo-diode to be swung in and out the light field 9 for light measurement.

What is claimed is:

1. A device for illuminating a limited defined area comprising:

a light source with a concave reflector device, the concave reflector device comprising a mirror with a curvature that concentrates the light from the light source on a first end surface of a cylindrical, transparent rod so that the light emitted from a second end surface of the rod is directed towards a lens for imaging the second end surface of the rod on the defined area which is to be illuminated, the lens being moveable so that the size of the defined area to be illuminated can be varied; and a light conducting means, wherein the device provides uniform irradiation on the defined area regardless of the size of the area and independently of correct positioning of the light source relative to a longitudinal center line of the device.

2. The device of claim 1 wherein the mirror is an elliptical mirror.

3. The device of claim 1 wherein the rod comprises a material which absorbs infrared radiation.

4. The device of claim 1 wherein the defined area is a pathological skin condition.

5. The device of claim 4 wherein the pathological skin condition is a cancerous tumor.

6. The device of claim 1 wherein in the light path between the light source and the rod there is placed a heat-reflecting filter and in front of the lens there are placed optical filters which define the part of the spectrum which is to be employed in the illumination.

7. The device of claim 6 wherein the light source with the reflector device, the heat-reflecting filter, the rod, the lens and the filters are mounted in plates provided on rails which thereby form a stand for the parts, with one or more of the plates being moveable on the rails.

8. The device of claim 7 wherein the stand is mounted in a first tube which is ventilated by a fan in a removable rear end of the first tube.

9. The device of claim 7 wherein the stand is mounted in a first tube, and wherein on the first tub e there is mounted a foot with a photo-diode on a moveable arm, which enables the photo-diode to be swung in and out of the defined area.

10. The device of claim 9 wherein the foot is moveable in relation to the first tube, the foot being attached to a second tube which runs through brackets which are attached to the first tube.

11. The device of claim 9 wherein the first tube is divided so that its rear end can be dismantled, thus facilitating the replacement of the light source.

* * * * *